United States Patent [19]

Savoca et al.

[11] Patent Number: 5,212,306
[45] Date of Patent: May 18, 1993

[54] AMINE-BORATE AND AMINE-BORON HALIDE COMPLEXES AS CATALYST COMPOSITIONS FOR THE PRODUCTION OF POLYURETHANES

[75] Inventors: Ann C. L. Savoca, Wyomissing; Mark L. Listemann, Whitehall, both of Pa.

[73] Assignee: Air Products and Chemicals, Inc., Allentown, Pa.

[21] Appl. No.: 947,237

[22] Filed: Sep. 18, 1992

[51] Int. Cl.$^5$ ............................................. C07D 251/34
[52] U.S. Cl. ................... 544/193; 521/104; 521/105; 502/200; 502/202
[58] Field of Search ................. 544/193; 521/104, 105; 502/200, 202

[56] References Cited

U.S. PATENT DOCUMENTS

| | | | |
|---|---|---|---|
| 3,127,404 | 3/1964 | Mascioli | 260/268 |
| 3,193,515 | 7/1965 | Mascioli | 260/2.5 |
| 3,635,848 | 1/1972 | Rambosek | 260/2.5 |
| 3,697,485 | 10/1972 | Rambosek et al. | 260/77.5 |
| 3,986,991 | 10/1976 | Kolakowski et al. | 260/2.5 |
| 4,151,334 | 4/1979 | Kan et al. | 521/105 |
| 4,503,226 | 3/1985 | Tang et al. | 544/193 |
| 4,536,490 | 8/1985 | Regelman | 544/193 |
| 4,537,961 | 8/1985 | Robin | 544/193 |
| 4,540,781 | 9/1985 | Barsa | 544/193 |
| 4,611,013 | 10/1986 | Ashida | 521/105 |
| 4,698,408 | 10/1987 | Goel et al. | 528/48 |
| 4,707,501 | 11/1987 | Petrella et al. | 521/115 |
| 5,086,081 | 2/1992 | Savoca et al. | 521/103 |

FOREIGN PATENT DOCUMENTS 2301554 9/1926 France.

OTHER PUBLICATIONS

Miller, Edgar, and Han Beat Burgi, "38 Complexes of 2,2′,2-Nitrilotriphenol" Helvetica Chimica Acta, vol. 70 No. (1987).

Colclough, T.; W. Gerrard and M. F. Lappert "Preparation, Stability and Complex Formation of Aryloxyboron Compounds" J. Chem. Soc. 1956, 3006.

Fieser, Mary and Louis F. Fieser "Reagents for Organic Synthesis" vol. 4 pp. 46-47.

Fieser, Mary and Louis F. Fieser "Reagents for Organic Synthesis" vol. 5 pp. 54-55.

*Primary Examiner*—Morton Foelak
*Attorney, Agent, or Firm*—Michael Leach; James C. Simmons; William F. Marsh

[57] ABSTRACT

A method for catalyzing the trimerization of an isocyanate and/or the reaction between an isocyanate and an active hydrogen-containing compound, the improvement which comprises employing a catalyst composition consisting essentially of the addition product of a tertiary amine urethane catalyst and a boron compound of the formula $$R_nBX_{3-n}$$

where
n represents 0, 1, 2 or 3,
X represents F, Cl, Br, OCOR′, OR″ or mixtures thereof, and
R, R′ and R″ independently represent $C_1$–$C_8$ alkyl, $C_5$–$C_8$ cycloalkyl, $C_6$–$C_{10}$ aryl or mixtures thereof.

11 Claims, No Drawings

AMINE-BORATE AND AMINE-BORON HALIDE COMPLEXES AS CATALYST COMPOSITIONS FOR THE PRODUCTION OF POLYURETHANES

TECHNICAL FIELD

The present invention relates to the use of tertiary amines as catalysts for producing polyurethanes.

BACKGROUND OF THE INVENTION

In the production of polyurethanes, it is often desirable to control the activity of the catalyst(s). The effect of controlled catalysis may be realized in improved reactivity profiles, for instance delayed initiation or accelerated cure. Such reaction rate control is of particular importance to the polyurethane molder, where it is important that the polyisocyanate/polyol mixture remain flowable for sufficient time to fill the mold properly, while maintaining or improving demold time. Controlled catalysis can also affect product distributions and significantly impact physical properties of the final polyurethane part.

Latent activity catalysts for initiation delay in polyurethane systems have been reported in the literature. One solution has been the use of ammonium salts of carboxylic acids, alone or in combination with other organometallic catalysts. The disadvantage of such materials is mainly their corrosiveness, but poor polyol masterbatch stability has also been reported in the presence of these acid blocked amine catalysts in U.S. Pat. No. 4,707,501. Bronsted acid blocked amine catalysts are prepared by reaction of a tertiary amine with a glycol borate acid. U.S. Pat. Nos. 3,193,515; 3,127,404 and FR 2,301,554 disclose the use of boric acid in the preparation of a blocked amine catalyst from triethylenediamine and a glycol borate acid. An ammonium salt of a quaternary borate anion results. The advantage of such catalyst composition is delayed activity and/or accelerated cure.

U.S. Pat. No. 5,086,081 describes reduced odor amine-boron compositions prepared from tertiary amine urethane catalysts and boric acid. These compositions are of reduced viscosity, low corrosiveness and impart improved reactivity profiles and physical properties during the production of polyurethane parts. These patents also mention the use of functional equivalents to boric acid (e.g., borate esters such as alkyl, dialkyl and trialkylborates in which the alkoxy groups hydrolyze to hydroxyl functionality in the presence of water).

Quaternary ammonium borates have been used to effect the concurrent trimerization/carbodiimidization of polyisocyanates (U.S. Pat. No. 4,611,013). The borates are prepared from boric acid, alcohols and quaternary ammonium hydroxide and, as such, are not derived from tertiary amines. Other examples of quaternary borate anions as polyurethane catalysts are given in U.S. Pat. Nos. 4,151,334; 3,697,485 and 3,635,848. Borate anions derived from borate esters have also been used for the production of isocyanurate and carbodiimide-isocyanurate foams. These borate anions are prepared by reaction of an alcohol with a borate ester (or boric acid) in the presence of an alkali metal.

The formation of amine-borate complexes has been reported in the literature and appears to depend on both steric and electronic factors. The trialkylborate formed from boric acid and nitrilotriethanol shows no reactivity toward moderate nitrogen nucleophiles, such as diazabicyclo[2.2.2]octane, whereas the related borate formed from 2,2',2"-nitrilotriphenol and boric acid was found to form an adduct with diazabicyclo[2.2.2]octane and other amines (*Helv. Chim Acta* 1987, 70, 499). Pyridine forms a 1:1 complex with tris-p-chlorophenylborate yet does not react with tris-2,4,6-trichlorophenylborate or 2,6-dimethylphenylborate (*J.Chem. Soc.* 1956, 3006).

Although acyl borates are known, e.g., boron tris(trifluoroacetate) (*Fieser and Fieser* 4, 46 and 5, 55), the use of acyl borate-amine complexes as urethane catalysts has not been investigated.

Boron halides are known to form stable complexes with amines. An example would be boron trifluoride-ethylamine (*Beil.* 4(2), 588). Such materials are well known epoxy curatives and have been used in formulations containing both polyisocyanates and polyepoxides (examples are U.S. Pat. Nos. 4,698,408 and 3,986,991).

SUMMARY OF THE INVENTION

The present invention provides a composition for catalyzing the trimerization of an isocyanate and/or its reaction with a compound containing a reactive hydrogen, e.g. the urethane reaction for making polyurethane. The catalyst composition consists essentially of a tertiary amine urethane catalyst in combination with a boron compound of the formula $$R_nBX_{3-n}$$

where
n represents 0, 1, 2 or 3,
X represents halide, OCOR', OR" or mixtures thereof, and
R, R' and R" independently represent alkyl, $C_1$–$C_8$ alkyl, $C_5$–$C_8$ cycloalkyl, $C_6$–$C_{10}$ aryl or mixtures thereof.

As an advantage of these catalyst compositions there is a significant improvement in reactivity profile during the production of a polyurethane. Most notably, these materials provide delayed initiation. Surprisingly, they provide delays comparable to or better than those provided by conventional Bronsted acid blocked amines and related amine-boric acid adducts. They also show improved solubility by comparison with amine-boric acid adducts.

DETAILED DESCRIPTION OF THE INVENTION

The catalyst compositions according to the invention can catalyze (1) the reaction between an isocyanate functionality and an active hydrogen-containing compound, i.e. an alcohol, an amine or water, especially the urethane (gelling) reaction to make polyurethanes and the blowing reaction of water with isocyanate to release carbon dioxide for making foamed polyurethanes, and (2) the trimerization of the isocyanate functionality to form polyisocyanurates. For the purpose of this invention, the term "polyurethane" is intended to include polyisocyanurate and polyisocyanurate/polyurethane.

The polyurethane products are prepared using suitable organic polyisocyanates well known in the art including, for example, hexamethylene diisocyanate, phenylene diisocyanate, toluene diisocyanate ("TDI") and 4,4'-diphenylmethane diisocyanate ("MDI"). Especially suitable are the 2,4- and 2,6-TDI's individually or together as their commercially available mixtures.

Other suitable isocyanates are mixtures of diisocyanates known commercially as "crude MDI", also known as PAPI, which contain about 60% of 4,4'-diphenylmethane diisocyanate along with other isomeric and analogous higher polyisocyanates. Also suitable are "prepolymers" of these polyisocyanates comprising a partially prereacted mixture of polyisocyanates and polyether or polyester polyols.

Illustrative of suitable polyols as a component of the polyurethane composition are the polyalkylene ether and polyester polyols. The polyalkylene ether polyols include the poly(alkylene oxide) polymers such as poly(ethylene oxide) and poly(propylene oxide) polymers and copolymers with terminal hydroxyl groups derived from polyhydric compounds, including diols and triols; for example, among others, ethylene glycol, propylene glycol, 1,3-butane diol, 1,4-butane diol, 1,6-hexane diol, neopentyl glycol, diethylene glycol, dipropylene glycol, pentaerythritol, glycerol, diglycerol, trimethylol propane and like low molecular weight polyols.

In the practice of this invention, a single high molecular weight polyether polyol may be used. Also, mixtures of high molecular weight polyether polyols such as mixtures of di- and tri-functional materials and/or different molecular weight or different chemical composition materials may be used.

Useful polyester polyols include those produced by reacting a dicarboxylic acid with an excess of a diol, for example, adipic acid with ethylene glycol or butanediol, or reacting a lactone with an excess of a diol such as caprolactone with propylene glycol.

In addition to the polyether and polyester polyols, the masterbatches, or premix compositions, frequently contain a polymer polyol. Polymer polyols are used in polyurethane foam to increase the foam's resistance to deformation, i.e. to increase the load-bearing properties of the foam. Currently, two different types of polymer polyols are used to achieve load-bearing improvement. The first type, described as a graft polyol, consists of a triol in which vinyl monomers are graft copolymerized. Styrene and acrylonitrile are the usual monomers of choice. The second type, a polyurea modified polyol, is a polyol containing a polyurea dispersion formed by the reaction of a diamine and TDI. Since TDI is used in excess, some of the TDI may react with both the polyol and polyurea. This second type of polymer polyol has a variant called PIPA polyol which is formed by the in-situ polymerization of TDI and alkanolamine in the polyol. Depending on the load-bearing requirements, polymer polyols may comprise 20–80% of the polyol portion of the masterbatch.

Other typical agents found in the polyurethane foam formulations include chain extenders such as ethylene glycol and butanediol; crosslinkers such as diethanolamine, diisopropanolamine, triethanolamine and tripropanolamine; blowing agents such as water, methylene chloride, trichlorofluoromethane, and the like; and cell stabilizers such as silicones.

A general polyurethane flexible foam formulation containing the catalyst composition according to the invention would comprise the following components in parts by weight (pbw):

| Flexible Foam Formulation | |
| --- | --- |
|  | Parts by Weight |
| Polyol | 20–80 |
| Polymer Polyol | 80–20 |

| Flexible Foam Formulation | |
| --- | --- |
|  | Parts by Weight |
| Silicone Surfactant | 1–2.5 |
| Blowing Agent | 2–4.5 |
| Crosslinker | 0.5–2 |
| Catalyst | 0.5–2 |
| Isocyanate Index | 70–115 |

The urethane catalyst composition consists essentially of the addition product, or complex, of a tertiary amine urethane catalyst and a boron compound of the general formula $$R_nBX_{3-n}$$

where n represents 0, 1, 2 or 3,

X represents halide (such as F, Cl and Br), OCOR', OR" or mixtures thereof, and

R, R' and R" independently represent $C_1-C_8$ alkyl, $C_5-C_8$ cycloalkyl, $C_6-C_{10}$ aryl or mixtures thereof.

Representative R, R' and R" groups include alkyl groups such as, for example, methyl, ethyl, butyl, 2-ethylhexyl and the like; cycloalkyl groups such as, for example, cyclopentyl, cyclohexyl and the like; and aryl groups such as, for example, phenyl, p-tolyl and the like.

Thus, carboxyl groups (—OCOR') on boron would include, for example, acetato, propionato, butyro, 2-ethylhexanato, benzoato and the like.

Alkoxy groups (—OR") would include, for example, methoxy, ethoxy, isopropoxy and the like; aryloxy groups (—OR") would include phenoxy and the like. Alkoxy groups would also include those derived from di- or polyhydric alcohols such ethylene glycol, diethylene glycol, propylene glycol and the like.

Exemplary of suitable boron compounds are trimethyl borate, tri-n-octyl borate, trimethylene borate, boron triacetate and boron trifluoride.

In the preferred boron compounds n is O, X is OR" and R" is $C_1-C_8$ alkyl, i.e., tri($C_1-C_8$ alkyl) borates.

It is contemplated that any tertiary amine suitable as a urethane catalyst can be used in making the amine-borate and amine-boron halide complex catalyst compositions. The suitable tertiary amine urethane catalyst may also contain hydroxy functionality. Illustrative of suitable tertiary amine urethane catalysts are pentamethyldiethylenetriamine, pentamethyldipropylenetriamine, bis(dimethylaminoethyl)ether, N,N-dimethylcyclohexylamine, N,N,N'-trimethyl-N'-hydroxyethylethylenediamine, triethylenediamine ("TEDA"), 4-dimethylaminopyridine, 1,8-diazabicyclo[5.4.0]undec-7-ene, 1,5-diazabicyclo[4.3.0]non-5-ene, N,N-dimethylethanolamine, N-ethylmorpholine, N-methylmorpholine, N-cetyl-N,N-dimethylamine, N-cocomorpholine, N-(N',N'-dimethylaminoethyl) morpholine, N,N,N'-trimethylaminoethylethanolamine, tris(3-dimethylaminopropyl)amine, 3-quinuclidinol and the like.

Typical molar ratios of tertiary nitrogen to boron in making the catalyst composition are from 1:0.01 to 1:100, preferably 1:0.1 to 1:10, most preferably 1:0.5 to 1:2 for acyclic amines and 1:0.5 to 1:1 for TEDA.

The complexes may be prepared by precipitation from an appropriate solvent. For example, a 1:1 molar complex of TEDA and $BF_3$ is prepared by the dropwise addition of $Et_2O-BF_3$ to a slight excess of triethylenediamine in anhydrous tetrahydrofuran. The complex precipitates from the reaction medium as a white solid.

The complexes are also easily prepared and more conveniently delivered as solutions in carriers such as alcohols, polyols, amines, polyamines, ethers, hydrocarbons, and chlorinated hydrocarbons. The preferred carriers are alcohols and polyols.

A catalytically effective amount of the catalyst composition is used in the polyurethane formulation. More specifically, suitable amounts of the catalyst composition may range from about 0.01 to 10 parts per 100 parts polyol in the polyurethane formulation.

The catalyst compositions may be used in combination with other tertiary amine and organotin urethane catalysts well known in the polyurethane art.

These catalyst compositions have the advantage of improved reactivity during the production of a polyurethane. Most notably, these materials provide delayed initiation. Surprisingly, they provide delays comparable to or better than those provided by conventional Bronsted acid blocked amines and the related amine-boric acid adducts. They also show improved solubility by comparison with amine-boric acid adducts.

COMPARATIVE EXAMPLE 1

This example shows the attempted preparation of a TEDA/boric acid solution in dipropylene glycol at 10 wt % amine and a 1:1 molar ratio of tertiary nitrogen to boron. A solution of TEDA (1.0 g, 8.8 mmol) in dipropylene glycol (6.8 g) was prepared. Boric acid (1.1 g, 17.6 mmol) was added all at once. The mixture was stirred vigorously at room temperature. Complete dissolution could not be achieved.

COMPARATIVE EXAMPLE 2

This example shows the attempted preparation of a TEDA/boric acid solution in dipropylene glycol at 8 wt % amine and a 1:1 molar ratio of tertiary nitrogen to boron. Boric acid (1.1 g, 17.8 mmol) was combined with dipropylene glycol (10 g) and heated, with vigorous stirring, to achieve near complete dissolution. Triethylenediamine (1.0 g, 8.9 mmol) was added and most of the amine dissolved within a few minutes. After 10 min, the solution began to cloud. The cloudy solution was allowed to cool, becoming very cloudy within 30 min. A white precipitate settled on standing.

EXAMPLE 3

This example demonstrates the improved solubility of amine-borate complexes by comparison with amine-boric acid adducts (Comparative Examples 1 and 2). TEDA/borate ester solutions were prepared at a 1:1 molar ratio of tertiary nitrogen to boron and an amine concentration equivalent to that used in Comparative Example 1. Reactants and weights are given in Table 1. In each case, a dipropylene glycol solution of TEDA was prepared at room temperature. The borate was added all at once and gave a clear, homogeneous solution.

TABLE 1

| | Reactant Weights | | | | |
|---|---|---|---|---|---|
| | TEDA | TOB[a] | TMB[a] | TMeB[a] | DPG |
| Example 3a 1:2 TEDA/TOB | 1.0 g | 7.0 g | | | 2.0 g |
| Example 3b 1:2 TEDA/TMB | 1.0 g | | 1.8 g | | 7.1 g |
| Example 3c 1:1 TEDA/TMeB | 1.0 g | | | 2.15 g | 6.75 g |

[a]TOB = tri-n-octyl borate, TMB = trimethyl borate, TMeB = trimethylene borate

EXAMPLE 4

This example compares the relative activity of several amine/borate complexes with Dabco 33 LV® catalyst (33 wt % TEDA in DPG; marketed by Air Products and Chemicals, Inc.) and DABCO® 8154 catalyst (a commercially available Bronsted acid blocked catalyst marketed by Air Products and Chemicals, Inc.). Also shown is TEDA/boric acid. A polyurethane foam formulation premix was prepared from the following:

| | |
|---|---|
| Pluracol 816 (EO-tipped polyether polyol) | 60 pphp |
| Pluracol 873 (SAN filled EO-tipped polyether polyol) | 40 pphp |
| DABCO® DC-5164 (silicone surfactant) | 1.0 pphp |
| DEOA-LF (85% diethanolamine in water) | 1.75 pphp |

For each foam, catalyst and water (enough to bring the total system water to 3.5 pphp) was added to 102.75 g of above premix in a 5" (12.7 cm) diameter, 10"(25.4 cm) tall paper can in amounts specified in Table 2 and the formulation was mixed well for 20 sec. Sufficient toluene diisocyanate (an 80/20 mixture of 2,4-TDI and 2,6-TDI) was added to make a 105 index foam (index=mole NCO/mole active hydrogen×100) and mixed well for 4 sec. The foam was allowed to rise freely, monitoring foam height with time.

TABLE 2

| | | | Free Rise Foam Height (cm) | | | | |
|---|---|---|---|---|---|---|---|
| Catalyst | Amount | Added Water | 13 sec | 18 sec | 25 sec | 31 sec | 37 sec |
| DABCO 33-LV | 1.00 g | 3.24 g | 13.0 | 21.1 | 26.9 | 30.5 | 32.5 |
| DABCO 8154 | 1.1 g | 3.24 g | 6.1 | 12.2 | 18.8 | 23.6 | 26.9 |
| TEDA/Boric acid | 1.32 g | 2.58 g | 5.6 | 10.2 | 16.0 | 21.3 | 25.1 |
| TEDA/TMB[a] | 3.3 g | 3.24 g | 8.4 | 15.2 | 21.1 | 25.1 | 27.7 |
| TEDA/TOB[a] | 3.3 g | 3.24 g | 7.1 | 13.0 | 18.5 | 23.1 | 25.9 |
| TEDA/TMeB[a] | 3.3 g | 3.24 g | 10.2 | 18.5 | 24.9 | 28.4 | 30.0 |
| 33LV/TMeB[b] | 1.0 g/ 0.72 g | 3.24 g | 8.4 | 15.2 | 20.8 | 24.6 | 26.9 |

[a]prepared according to Example 3
[b]added DABCO 33-LV and trimethylborate separately to formulation The data show that amine borate complexes delay foam rise relative to the unblocked amine catalyst, DABCO 33-LV TEDA. The extent of delay appears to be dependent upon the borate structure as well as the method of delivery of the borate into the formulation. The last two entries in the table compare TEDA/TMeB delivered as a formulated catalyst solution and delivered as the complex components, triethylenediamine and trimethylene borate, the latter showing greater delay according to this test method.

EXAMPLE 5

A more general and quantitative technique for measuring catalyst activity is given in this example. Here the relative catalytic activity of various combinations of TEDA and borate esters or boron trifluoride are compared with two control catalysts, a 1:2 molar combination of TEDA with boric acid and DABCO 8154 catalyst using a polyurethane model. All catalysts were compared at an equimolar amine level. DABCO 8154 catalyst was used as received. The TEDA/BF$_3$ was prepared according to the procedure of Brown and Singaram (*Inorg. Chem* 1980, 19, 455) and delivered as a solid complex. All amine/borate combinations were delivered as their individual components. The rate of isocyanate consumption as a function of time was measured using a formulation similar to that of Example 4, but containing monofunctional reactants. Reaction samples drawn at the indicated times were quenched with dibutylamine and analyzed by liquid chromatography. The catalysts were compared on an equimolar basis corresponding to a loading of 0.70 parts per hundred parts of DABCO 33 LV ® catalyst (33 wt % TEDA in DPG) set forth in Example 4. Table 3 summarizes the results.

TABLE 3

| Catalyst | % NCO Conversion Time (min) | | | | | | |
|---|---|---|---|---|---|---|---|
| | 0.5 | 1.0 | 2.0 | 3.0 | 4.0 | 6.0 | 8.0 |
| TEDA | 36.8 | 56.5 | 72.6 | 79.2 | 81.9 | 86.7 | 88.8 |
| DABCO 8154 | 31.5 | 52.6 | 69.1 | 75.3 | 78.3 | 81.9 | 84.6 |
| TEDA/Boric (1:2 molar) | 30.7 | 50.3 | 66.5 | 71.9 | 75.3 | 78.8 | 80.6 |
| TEDA/TOB$^a$ (1:2 molar) | 29.6 | 51.7 | 70.7 | 77.7 | 80.7 | 83.9 | 87.0 |
| TEDA/TMB$^a$ (1:2 molar) | 28.0 | 50.2 | 69.7 | 76.1 | 79.5 | 82.7 | 84.8 |
| TEDA/T-MeB$^a$ (1:1 molar) | 25.8 | 46.9 | 66.6 | 73.7 | 77.0 | 80.6 | 82.4 |
| TEDA/BF$_3^a$ (1:1 molar) | 6.3 | 13.6 | 27.9 | 41.6 | 52.9 | 63.4 | 69.2 |

$^a$TOB = tri-n-octyl borate, TMB = trimethyl borate, TMeB = trimethylene borate The data in Table 2 show the delay afforded by TEDA/borate and TEDA/BF$_3$ complexes by comparison with TEDA/boric acid. The TEDA/BF$_3$, expected to be the strongest complex, shows the most significant delay. All of the boron based complexes show some delay relative to the Bronsted acid blocked TEDA (DABCO 8154 catalyst) and tremendous delay by comparison with TEDA itself.

Surprisingly, an additional advantage afforded by the TEDA/borate complexes is improved isocyanate conversion late in the reaction, despite the initial delay. All show improved % NCO conversion relative to TEDA/boric acid after 2.0 min; TEDA/TOB and TEDA/TMB also achieve greater isocyanate conversion than DABCO 8154 catalyst.

STATEMENT OF INDUSTRIAL APPLICATION

The present invention provides an amine catalyst composition for making polyurethane foam products.

We claim:

1. In a method for catalyzing the trimerization of an isocyanate and/or the reaction between an isocyanate and an active hydrogen-containing compound, the improvement which comprises employing a catalyst composition consisting essentially of the addition product of a tertiary amine urethane catalyst and a boron compound of the formula $$R_nBX_{3-n}$$

where
n represents 0, 1, 2 or 3,
X represents halide, OCOR', OR'' or mixtures thereof, and
R, R' and R'' independently represent C$_1$–C$_8$ alkyl, C$_5$–C$_8$ cycloalkyl, C$_6$–C$_{10}$ aryl or mixtures thereof.

2. The method of claim 1 in which the catalyst composition is employed in combination with a tertiary amine urethane catalyst or an organotin urethane catalyst, or both.

3. The method of claim 1 in which the tertiary amine is pentamethyldiethylenetriamine, pentamethyldipropylenetriamine, bis(dimethylaminoethyl) ether, N,N-dimethylcyclohexylamine, 4-dimethylaminopyridine, 1,8-diazabicyclo[5.4.0]undec-7-ene, 1,5-diazabicyclo[4.3.0]non-5-ene, N-ethylmorpholine, N-methylmorpholine, N-cetyl-N,N-dimethylamine, N-cocomorpholine, N-(N,N-dimethylaminoethyl)morpholine, tris(3-dimethylaminopropyl)amine, triethylenediamine, N,N,N'-trimethyl-N'-hydroxyethylethylenediamine, N,N-dimethylethanolamine, N,N,N'-trimethylaminoethylethanolamine or 3-quinuclidinol.

4. The method of claim 1 in which the tertiary amine is triethylenediamine.

5. The method of claim 4 in which the tertiary nitrogen to boron is a molar ratio of 1:0.5 to 1:1.

6. The method of claim 1 in which the boron compound is trimethylborate, tri-n-octyl borate, trimethylene borate, boron triacetate or boron trifluoride.

7. The method of claim 1 in which in the boron compound is a tri(C$_1$–C$_8$ alkyl) borate.

8. The method of claim 4 in which in the boron compound is a tri(C$_1$–C$_8$ alkyl) borate.

9. The method of claim 4 in which the boron compound is trimethyl borate, tri-n-octyl borate or trimethylene borate.

10. The method of claim 1 in which the tertiary nitrogen to boron molar ratio of the catalyst composition is 1:0.1 to 1:10.

11. The method of claim 1 in which the tertiary nitrogen to boron molar ratio of the catalyst composition is 1:0.5 to 1:2.

* * * * *